US009464987B2

(12) United States Patent
Gillespie (10) Patent No.: US 9,464,987 B2
(45) Date of Patent: Oct. 11, 2016

(54) DEVICE AND SYSTEM FOR MONITORING THE SLUDGE LEVEL IN A SEPTIC TANK SYSTEM (71) Applicant: Andrew Gillespie, South Easton, MA (US)

(72) Inventor: Andrew Gillespie, South Easton, MA (US)

( * ) Notice: Subject to any disclaimer, the term of this patent is extended or adjusted under 35 U.S.C. 154(b) by 116 days.

(21) Appl. No.: 14/479,416

(22) Filed: Sep. 8, 2014

(65) Prior Publication Data

US 2016/0069818 A1     Mar. 10, 2016

(51) Int. Cl.
G01N 21/94     (2006.01)
G01N 21/59     (2006.01)
G01N 21/85     (2006.01)
G01F 23/00     (2006.01)

(52) U.S. Cl.
CPC .......... G01N 21/59 (2013.01); G01N 21/8507 (2013.01); *G01F 23/00* (2013.01); *G01N 2201/062* (2013.01)

(58) Field of Classification Search
CPC .......... C01N 21/94; G01N 2201/062; G01N 21/59; G01F 23/00; G01F 23/22
USPC ............ 356/436, 440, 402, 409, 412, 414; 250/357.1, 343, 573
See application file for complete search history.

(56) References Cited

U.S. PATENT DOCUMENTS

| | | | | | |
|---|---|---|---|---|---|
| 4,715,966 A | * | 12/1987 | Bowman | ................. | C02F 3/006 210/532.2 |
| 4,719,359 A | * | 1/1988 | Rose | ..................... | G01F 23/292 250/573 |
| 5,026,993 A | * | 6/1991 | James | ................... | G01F 23/292 250/343 |
| 5,208,465 A | * | 5/1993 | Jacobson | ............... | G01N 21/17 250/573 |
| 5,712,710 A | * | 1/1998 | Karakus | ............ | G01N 21/8507 250/576 |
| 6,012,020 A | * | 1/2000 | Gardell | .................... | C02F 3/006 367/87 |
| 6,217,752 B1 | * | 4/2001 | Coots | .................... | G01F 23/185 116/109 |
| 2009/0008338 A1 | * | 1/2009 | Dunbar | ................... | E03F 11/00 210/741 |
| 2010/0149539 A1 | * | 6/2010 | Kwak | ..................... | B01D 21/32 356/440 |
| 2013/0317766 A1 | * | 11/2013 | Decker | ............... | G01F 23/0076 702/55 |

FOREIGN PATENT DOCUMENTS

FR     2797650 A1 *    2/2001     .............. E03F 11/00

* cited by examiner

*Primary Examiner* — Sang Nguyen
(74) *Attorney, Agent, or Firm* — Bay State IP, LLC (57) ABSTRACT A device and system for monitoring the sludge level in a septic system tank, wherein a plurality of monitoring devices are positioned within a septic tank being monitored. Each monitoring device preferably includes a base unit, and a probe arm extending down from the base unit into the septic tank, wherein each probe arm includes a light emitting diode arm and a dark sensor photocell arm.

14 Claims, 8 Drawing Sheets

DEVICE AND SYSTEM FOR MONITORING THE SLUDGE LEVEL IN A SEPTIC TANK SYSTEM

BACKGROUND OF THE INVENTION

1. Field of the Invention

The instant invention relates generally to monitoring systems, and more particularly to a device and system to monitor the level of a sludge in septic tank to alert an individual when the system should be pumped.

2. Description of the Related Art

Septic tanks are used as an alternative to sewer systems in locations where those systems are not available. A septic tank generally consists of a tank connected to an inlet wastewater pipe at one end and a septic drain field at the other end. Waste water enters the tank through the inlet and solids to settle to the bottom of the tank while scum floats and is allowed to exit to the septic drain field.

Septic tanks despite being a good alternative to a sewer system do come with certain limitations. If the liquid in a septic tank fills to a level at or above the incoming sewer drain line, the sewer drain line may back up and cause potentially harmful sewage to flood a house or building. A sewage flood can be hazardous to the health of people and animals, and can also cause extensive property damage. Furthermore, the solid levels in the tank can rise to the level of the outlet pipe thus depositing solid waste into the drain field. The presence of suspended solids in the drain field will, over time, result in the field becoming clogged by the solids to such an extent that it can no longer absorb and disperse the polluted water. This failure will typically be evidenced by pollution of ground and surface water. This can be an expensive problem to fix. In order to prevent these issues often requires the septic tank to be pumped before eat reaches a level resulting in failure of the system.

The most common method for determining the levels of the septic tank is a visual inspection of the tank. This requires the septic tank cover to be removed which can be an exhaustive process that yields an inaccurate reading. Another common method is to remove the access cover to the septic tank and to measure the depth of each of the three layers by pushing a "flapper stick" into the tank. The flapper stick is configured so that it can be used to gauge the bottom of the tank. Direct observation of the stick after removal indicates the depth of the bottom sediment. The process of removing the septic tank cover and removing reading the stick can be a very unpleasant task as it exposes the operator to the open septic system. An additional limitation of these testing procedures is tester, typically the owner of the property, must be present to test the levels of the tank. Septic tanks are common in many vacation homes as they are often in more remote locations requiring the use of a septic system. As a result the owner will often not be at the property to test the system.

SUMMARY OF THE INVENTION

The instant system and method, as illustrated herein, is clearly not anticipated, rendered obvious, or even present in any of the prior art mechanisms, either alone or in any combination thereof. Thus the several embodiments of the instant system and method are illustrated herein.

In one aspect of the instant invention, a monitoring device and system is disclosed to monitor the level of sludge in a septic tank, wherein each monitoring device utilizes light emitting diode and dark photo sensors to determine the level of sludge through the transmission of signals and alarms remotely, according to the measurement taken.

It is an object of the invention to provide a septic tank sludge level monitoring system.

It is a further object of the invention to provide the user a notification of sludge levels in the septic tank.

It is another object of the invention to provide a septic tank sludge level monitoring system a user can install.

It is another object of the invention to provide a system that is adaptable to a variety of pipe configurations.

There has thus been outlined, rather broadly, the more important features of a device and system to monitor the level of sludge in a septic tank system in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

These together with other objects of the invention, along with the various features of novelty, which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

DETAILED DESCRIPTION OF THE SEVERAL EMBODIMENTS

The detailed description set forth below in connection with the appended drawings is intended as a description of presently preferred embodiments of the invention and does not represent the only forms in which the present invention may be constructed and/or utilized. The description sets forth the functions and the sequence of steps for constructing and operating the invention in connection with the illustrated embodiments.

Figure 1A:
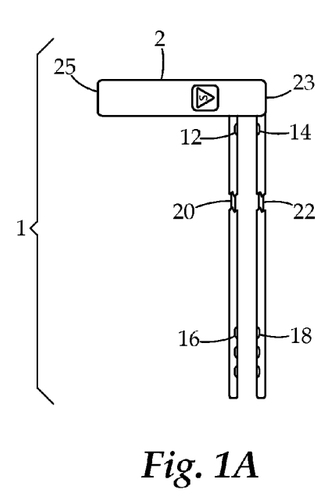
FIG. 1A illustrates a front view of one embodiment of the instant invention, wherein the monitoring device is able to mount on a vertical pipe.
Figure 1B:
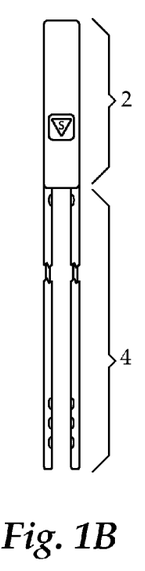
FIG. 1B illustrates a front view of another embodiment of the instant invention, wherein the monitoring is able to mount on a horizontal pipe.
Figure 7:
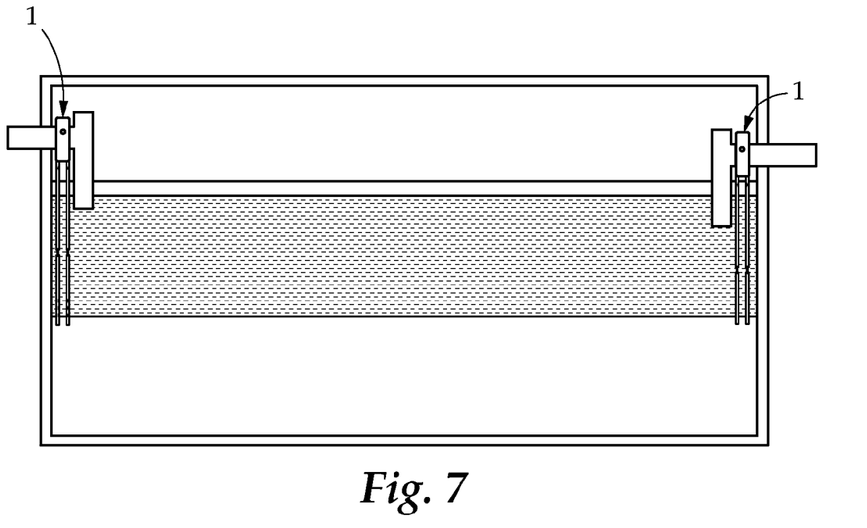
FIG. 7 illustrates a cross sectional view of a septic tank, wherein a plurality of monitoring devices are located within the tank and in operation.

FIGS. 1A-1B illustrate one embodiment of a device and system for monitoring the level of sludge in a septic tank, wherein a monitoring device 1 comprises a base unit 2 for preferably securing the monitoring device 1 to an outflow or inflow pipe (see FIG. 7) within a septic tank (see FIG. 7). The monitoring device 1 further comprises a probe arm 4, wherein the probe arm 4 extends downwardly from a lower end 23 of the base unit 2. In the embodiment shown in FIG. 1A, the base unit 2 is in a perpendicular orientation with respect to the probe arm 4, thereby enabling the monitoring device 1 to be mounted on a vertical pipe in the septic tank (i.e. wherein the pipe is oriented parallel to the probe arm 4 of the monitoring device 1). In one embodiment, the probe arm 4 further comprises a light emitting diode ("LED") arm 12 and a dark sensor photocell arm 14, wherein the LED arm 12 and the photocell arm 14 are contained within the probe arm 4. Preferably, the LED probe arm 12 and the dark sensor photocell arm 14 are oriented parallel to one another and extend vertically downward. The LED probe arm 12 further comprises a plurality of LED probes 16; the dark sensor photocell arm 14 further comprises a plurality of dark sensor photocells 18 wherein each dark sensor photocell 18 is paired with a corresponding LED probe 16. In one embodiment, each corresponding LED probe 16 and the dark sensor photocell 18 are equidistantly disposed along the LED probe arm 12 and the dark sensor photocell arm 14 so that each are positioned at the same distance from the bottom of the septic tank. In a preferred embodiment the LED probe 16 and the corresponding dark sensor photocell 18 are positioned within the septic tank at a level that is equivalent to the septic tank being one third full of sludge or any other similar debris. Additionally, in one embodiment, the LED probe arm 12 and the dark sensor photocell arm 14 each contain further comprises a plurality of circuit wires 20, 22 respectively to transmit a signal and/or alarm remotely to an individual operator. In the embodiment shown in FIG. 1B, the base unit 2 is in a parallel orientation with respect to the probe arm 4, thereby enabling the monitoring device 1 to be mounted on a horizontal pipe in the septic tank (i.e. wherein the pipe is oriented perpendicular to the probe arm 4 of the monitoring device 1).

Figure 2A:
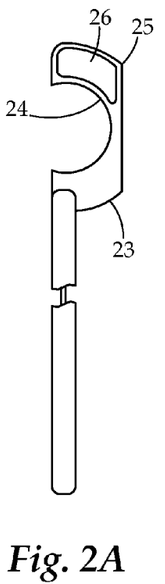
FIG. 2A illustrates a side view of one of embodiment of the monitoring device for mounting on the side of a pipe.
Figure 2B:
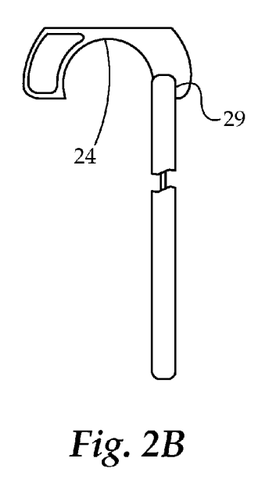
FIG. 2B illustrates a side view one embodiment of the monitoring device for mounting on the top of a pipe.

FIGS. 2A-2B illustrates side views of one embodiment of the monitoring device 1, wherein the base unit 2 further comprises an inner radius 24 and a cavity 26. Preferably, the inner radius 24 of the base unit 2 possesses a radius substantially equal to the radius of the corresponding inflow or outflow pipe to which the monitoring device 1 will be affixed in order to create a snap fit between the pipe and the monitoring device 1; creating a snap fit simplifies the installation process of the monitoring device 1. In one embodiment, the cavity 26 located within the base unit 2 allows for the snap fit to be achieved by reducing the rigidity of the cavity of the base unit 2 thereby allowing for a slight tolerance of the inner radius 24 so that the monitoring device 2 accepts the pipe to which the monitoring device 1 is affixed. In the embodiment shown in FIG. 2B, the base unit 2 is in a perpendicular orientation with respect to the probe arm 4, thereby enabling the monitoring device 1 to be mounted on the top of a pipe in the septic tank. Preferably, the base unit 2 snaps onto a corresponding pipe via an overcam (over-center) hanger opening, wherein the radius of the base unit 2 matches the radius of the attached corresponding pipe. Additionally, the opening of the base unit 2 is narrower than the pipe to provide the mechanical force as the base unit 2 is forced open when the base unit 2 is being pushed onto the pipe unit it pops over the pipe and subsequently snaps onto the pipe. In yet another embodiment, a joint 29 is present at the lower end 23 of the base unit 2, where the base unit 2 meets the probe arm 4 to enable various attachment orientation designs.

Figure 3:
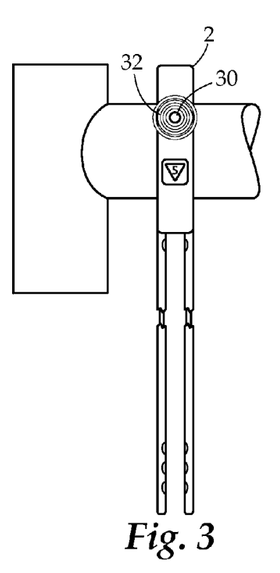
FIG. 3 illustrates a front view of the monitoring device mounted on a horizontal pipe.

FIG. 3 illustrates a preferred embodiment of the monitoring device 1 affixed to an inflow or outflow pipe in the septic tank. In one embodiment, the base unit 2 further comprises an "ON" button 30; the "ON" button 30 turns the monitor device 1 on for operation. Additionally, the "ON" button 30 further comprises an indicator LED 32, wherein the indicator LED 32 displays a powered on monitoring device 1 when it is illuminated green.

Figure 4:
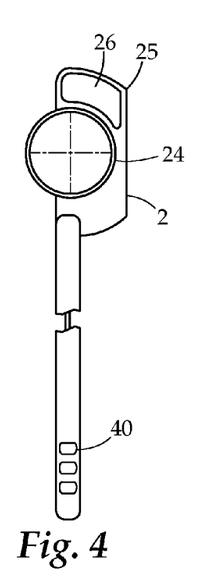
FIG. 4 illustrates a side view of the monitoring device mounted on a horizontal pipe.

FIG. 4 illustrates a cross sectional view of a preferred embodiment of the monitoring device 1 installed on a horizontal pipe in a septic tank. In this embodiment, the base unit 2 is affixed to a horizontal pipe through use of the inner radius 24 creating a snap fit. Furthermore, in one embodiment, the LED arm 12 and the dark sensor photocell arm 14 each comprises a plurality of windows 40 along the respective arms 12, 14, wherein each window 40 allows for each of the LED probes 16 and the dark sensor photocells 18 to be submerged in the septic tank and remain clean while also being able to transmit through each window 40. In one embodiment, each window 40 covers the LED probes 16 and the dark sensor photocells 18 respectively, yet still allows for the transmission of signals between the LED probes 16 and the dark sensor photocells 18.

Figure 5:
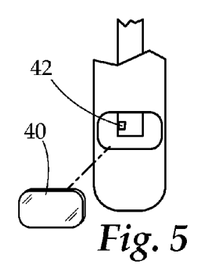
FIG. 5 illustrates one embodiment of a light emitting diode sensor along with a LED circuit diagram located on the monitoring device.

FIG. 5 illustrates an internal view of one embodiment of the LED probe 16. In this embodiment, the LED probe 16 further comprises an LED circuit 42. The LED circuit 42 provides power to the LED probes 16 as well as allowing for the transfer of signals.

Figure 6:
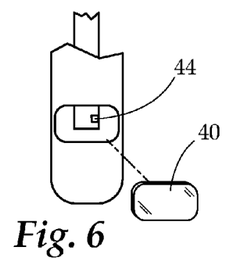
FIG. 6 illustrates one embodiment of a photocell sensor with a photocell circuit diagram located on the monitoring device.

FIG. 6 illustrates an internal view of one embodiment of the dark sensor photocell 18. The dark sensor photocell 18 further comprises a dark sensor photocell circuit 44. The dark sensor photocell circuit 44 provides power to the dark sensor photocells 18 as well as allowing for the transfer of signals.

FIG. 7 illustrates a preferred embodiment of the system for monitoring the level of sludge in a septic tank system, wherein a plurality of monitoring devices 1 have been installed on various inflow and outflow pipes. The preferred embodiment utilizes one monitoring device 1 affixed to an inflow pipe and one monitoring device 1 affixed to an outflow pipe. Each monitoring device 1 may be fixed to either the vertical or horizontal portions of the inflow or outflow pipes utilizing the base unit 2. Furthermore, the probe arm 4 extends downwardly from the base unit 2 in a direction perpendicular with respect to the bottom of the tank.

Figures 8, 9:
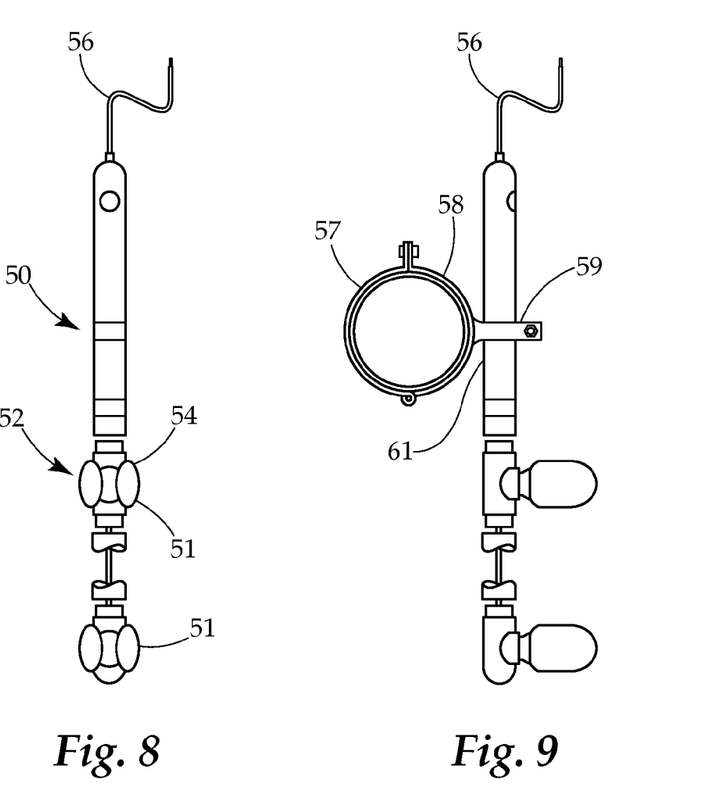
FIG. 8 illustrates a front view of an alternate embodiment of the monitoring device comprising at least one sensor arm.
FIG. 9 illustrates a side view of an alternate embodiment of the monitoring device comprising at least one sensor arm and at least one clamp.

FIG. 8 illustrates an alternate embodiment of the monitoring device 1. In this embodiment the monitoring device 1 comprises a sensor arm 50 that extends downwardly into the septic tank in a direction perpendicular with respect to the bottom of the septic tank. The sensor arm 50 comprises a plurality of sensor housings 51 wherein each sensor housing 51 further comprises one LED sensor 52 and one photocell sensor 54. The sensor housings 51 are spaced vertically along the length of the sensor arm 50. The vertical positioning of the sensor housings 51 is selected by the user in order to achieve the proper readings desired. The sensor arm 50 further comprises a wire 56 at the top end of the sensor arm 50. The wire 56 comprises a wire outer casing, a plurality of signal wires, and a plurality of power wires. The wire outer casing shields the plurality of signal wires and plurality of power wires from damage.

FIG. 9 illustrates an alternate embodiment of the monitoring device 1 further comprising a mounting device 57. The device 57 further comprises a pipe clamp 58 and a holding arm clamp 59; the pipe clamp 58 and the holding arm clamp 59 are integrally coupled and oriented so that the sensor arm 50 is oriented vertically and pointing downward. In this embodiment, a hinged joint 61 is present between the pipe clamp 58 and the arm clamp 59 to allow for the monitoring device 1 to be utilized on both vertical and horizontal pipes.

Figure 10:
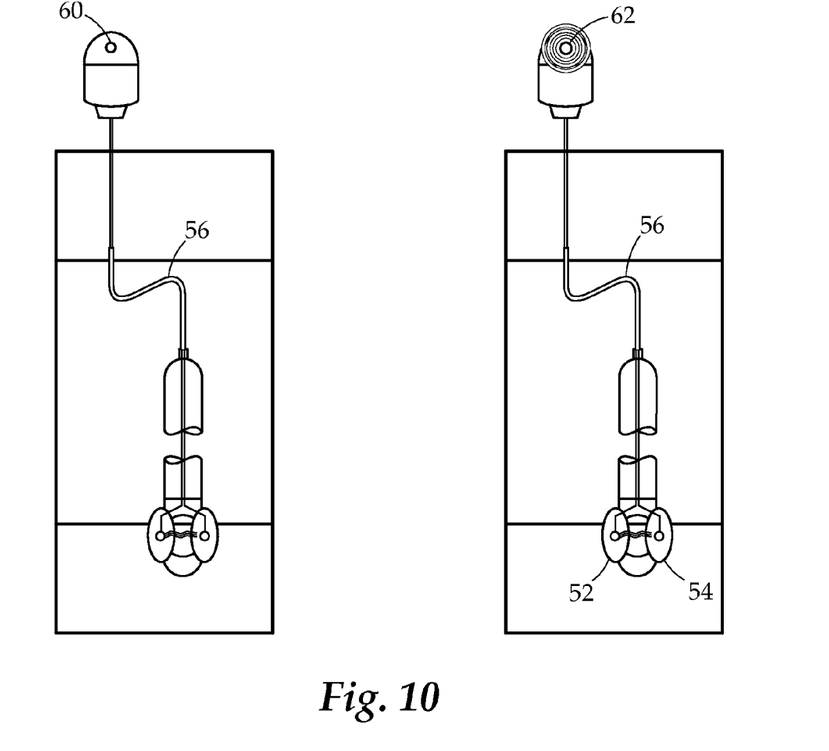
FIG. 10 illustrates a front view of an alternate embodiment of monitoring device comprising an additional above ground solar array.

FIG. 10 illustrates an alternate embodiment of the monitoring device 1 further comprising an above ground solar array 60, wherein the solar array 60 further comprises an indicator light 62. In this embodiment, the solar array 60 provides power to the monitoring device 1 through a connecting wire 56. The indicator light 62 provides status indicators to the user. In one embodiment a non-illuminated indicator light 62 indicates a properly functioning system. In one embodiment the indicator light 62 will illuminate red to tell the user to pump the septic tank and will indicate orange to tell the user the septic tank will need to be pumped soon.

Figure 11:
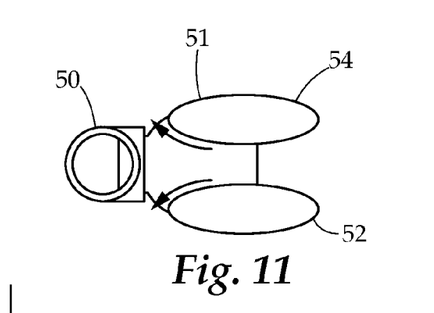
FIG. 11 illustrates a top view of an alternate embodiment of the LED and photocell sensors of the monitoring device.
Figure 12:
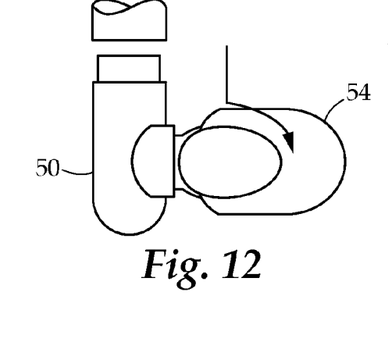
FIG. 12 illustrates a side view of an alternate embodiment of the LED and photocell sensors of the monitoring device.
Figure 13:
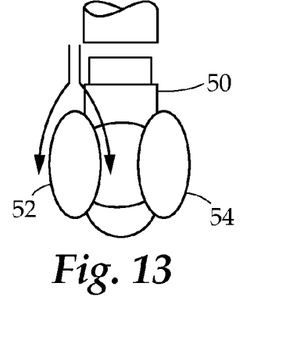
FIG. 13 illustrates a front view of an alternate embodiment of the LED and photocell sensors of the monitoring device.

FIGS. 11-13 illustrate one embodiment of the sludge level monitoring system 1 wherein the sensor housing 51 comprises a LED sensor 52 and the photocell sensor 54. In this embodiment, the LED sensor 52 is affixed to the left side of the sensor housing 51 and the photocell sensor 54 is affixed to the right side of the sensor housing 51. The alignment of the LED sensor 52 and the photocell sensor 54 inside the sensor housing 51 creates a gap between the LED sensor 52 and the photocell sensor 54 in which liquid and debris pass for detection. The LED sensor 52 and photocell sensor 54 are preferably round in shape so that falling debris falls around the sensor housings 51 but does not accumulate resulting in inaccurate readings.

Figure 14:
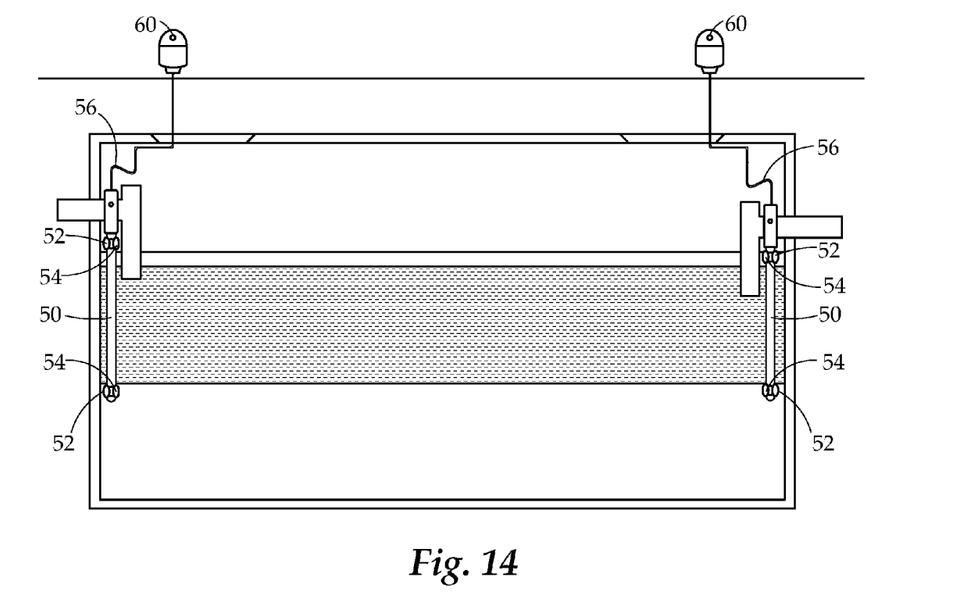
FIG. 14 illustrates a cross-sectional view of a septic tank, wherein an alternate embodiment of monitoring devices are installed and in operation.

FIG. 14 illustrates use of an alternate embodiment of the monitoring device 1 in use during operation. In this embodiment, the single sensor arm 50 extends downward into the different levels of the septic tank. Preferably, locations of the LED sensor housing 51 are selected to optimize readings; the readings are transferred to the solar array 60 which contains the indicator light 62.

In operation, the instant invention relates to a device and system for monitoring the level of sludge in a septic tank, wherein at least one monitoring device 1 may be located within a corresponding septic tank. In one embodiment, upon installation of the instant invention is powered on and synced with a modem. The home or business owner must access a web page and enter the unique product code to register the system. Subsequent, the operator of the system is then guided through an account set-up and provided with the account information. At this point the system may be programmed via a calendar or placed in auto-mode. Preferably, the monitoring system will have a minimal default setting to ensure a base level of measurement; the user may change any calendar and other settings via the smart phone app or webpage. The system is preferably always in a low-power "sleep" mode until a timer wakes each monitoring device 1 to perform a test. One such test involves the LED flashing on and the photocell on the probe arm 4 reading the level of light emitted. If the photocell reads a given level of light above a pre-determined number, then the system determines that the liquid in the tank is clear, and the monitoring device 1 sends a "green/OK" signal to all interfaces registered to receive data, including an interface that may also be located inside the operator's home or business. As time progresses, and with each subsequent test the system will indicate the reducing light levels and send appropriate updated message as the septic tank water becomes more saturated with falling debris, such as "amber/warning/pump soon" to all interfaces. In a "pump soon" scenario the system will enter an auto-tracking mode and test via a predetermined program, over-riding the operator's schedule to ensure a much closer monitoring as the need to empty the septic tank draws closer. In a scenario when the system arms, the LED illuminates, and the photocell receives little or no light then the device will send a "red/danger/pump now message to all interfaces.

Figure 15A:
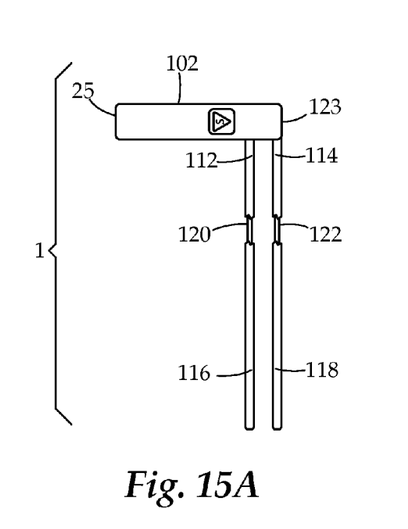
FIGS. 15A-15B illustrate yet another embodiment of a device and system for monitoring the level of sludge in a septic tank.
Figure 15B:
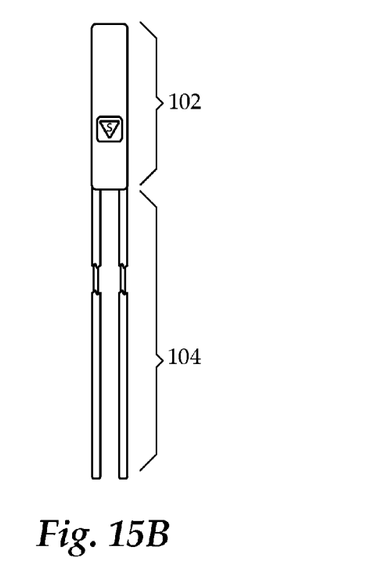

FIGS. 15A-15B illustrate yet another embodiment of a device and system for monitoring the level of sludge in a septic tank, wherein a monitoring device 100 comprises a base unit 102 for preferably securing the monitoring device 100 to an outflow or inflow pipe (see FIG. 7) within a septic tank (see FIG. 7). The monitoring device 100 further comprises a probe arm 104, wherein the probe arm 104 extends downwardly from a lower end 123 of the base unit 102. In the embodiment shown in FIG. 15A, the base unit 102 is in a perpendicular orientation with respect to the probe arm 104, thereby enabling the monitoring device 100 to be mounted on a vertical pipe in the septic tank (i.e. wherein the pipe is oriented parallel to the probe arm 104 of the monitoring device 100). In one embodiment, the probe arm 104 further comprises a light emitting diode ("LED") arm 112 and a dark sensor photocell arm 114, wherein the LED arm 112 and the photocell arm 114 are contained within the probe arm 104. Preferably, the LED probe arm 112 and the dark sensor photocell arm 114 are oriented parallel to one another and extend vertically downward. The LED probe arm 112 further comprises a plurality of LED probes 116; the dark sensor photocell arm 114 further comprises a plurality of dark sensor photocells 118 wherein each dark sensor photocell 118 is paired with a corresponding LED probe 116. In one embodiment, each corresponding LED probe 116 and the dark sensor photocell 118 are equidistantly disposed along the LED probe arm 112 and the dark sensor photocell arm 114 so that each are positioned at the same distance from the bottom of the septic tank. In a preferred embodiment the LED probe 116 and the corresponding dark sensor photocell 118 are positioned within the septic tank at a level that is equivalent to the septic tank being one third full of sludge or any other similar debris. Additionally, in one embodiment, the LED probe arm 112 and the dark sensor photocell arm 114 each contain further comprises a plurality of circuit wires 120, 122 respectively to transmit a signal and/or alarm remotely to an individual operator. In the embodiment shown in FIG. 15B, the base unit 102 is in a parallel orientation with respect to the probe arm 104, thereby enabling the monitoring device 100 to be mounted on a horizontal pipe in the septic tank (i.e. wherein the pipe is oriented perpendicular to the probe arm 104 of the monitoring device 100).

Figure 16A:
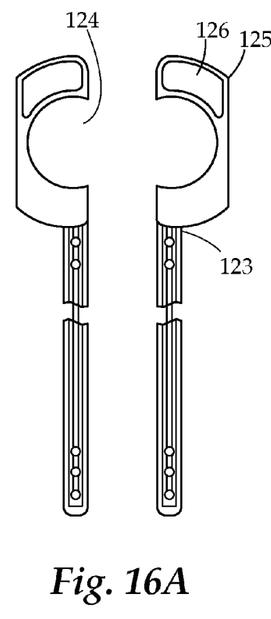
FIGS. 16A-16B illustrates side views of one embodiment of the monitoring device wherein the base unit comprises an inner radius and a cavity.
Figure 16B:
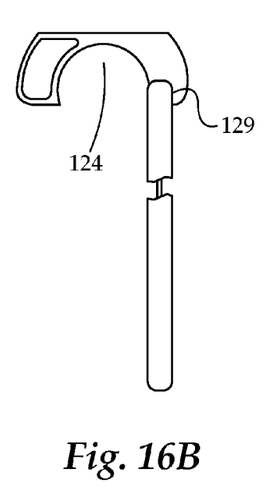

FIGS. 16A-16B illustrates side views of one embodiment of the monitoring device 100, wherein the base unit 102 further comprises an inner radius 124 and a cavity 126. Preferably, the inner radius 124 of the base unit 102 possesses a radius substantially equal to the radius of the corresponding inflow or outflow pipe to which the monitoring device 100 will be affixed in order to create a snap fit between the pipe and the monitoring device 100; creating a snap fit simplifies the installation process of the monitoring device 100. In one embodiment, the cavity 126 located within the base unit 102 allows for the snap fit to be achieved by reducing the rigidity of the cavity of the base unit 102 thereby allowing for a slight tolerance of the inner radius 124 so that the monitoring device 102 accepts the pipe to which the monitoring device 100 is affixed. In the embodiment shown in FIG. 16B, the base unit 102 is in a perpendicular orientation with respect to the probe arm 104, thereby enabling the monitoring device 100 to be mounted on the top of a pipe in the septic tank. Preferably, the base unit 102 snaps onto a corresponding pipe via an overcam (over-center) hanger opening, wherein the radius of the base unit 102 matches the radius of the attached corresponding pipe. Additionally, the opening of the base unit 102 is narrower than the pipe to provide the mechanical force as the base unit 102 is forced open when the base unit 102 is being pushed onto the pipe unit it pops over the pipe and subsequently snaps onto the pipe. In yet another embodiment, a joint 129 is present at the lower end 123 of the base unit 102, where the base unit 102 meets the probe arm 104 to enable various attachment orientation designs.

Figure 17:
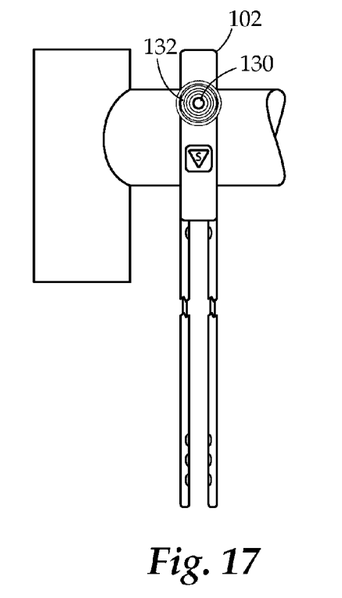
FIG. 17 illustrates a preferred embodiment of the monitoring device affixed to an inflow or outflow pipe in the septic tank.

FIG. 17 illustrates a preferred embodiment of the monitoring device 100 affixed to an inflow or outflow pipe in the septic tank. In one embodiment, the base unit 102 further comprises an "ON" button 130; the "ON" button 130 turns the monitor device 100 on for operation. Additionally, the "ON" button 130 further comprises an indicator LED 132, wherein the indicator LED 132 displays a powered on monitoring device 100 when it is illuminated green.

Figure 18:
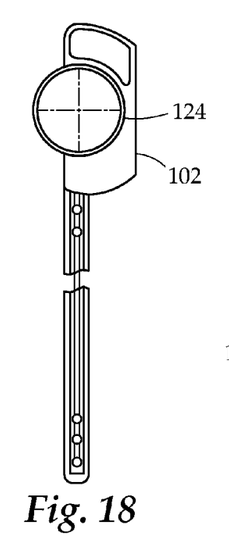
FIG. 18 illustrates a cross sectional view of a preferred embodiment of the monitoring device installed on a horizontal pipe in a septic tank.

FIG. 18 illustrates a cross sectional view of a preferred embodiment of the monitoring device 100 installed on a horizontal pipe in a septic tank. In this embodiment, the base unit 102 is affixed to a horizontal pipe through use of the inner radius 124 creating a snap fit.

Figure 19A:
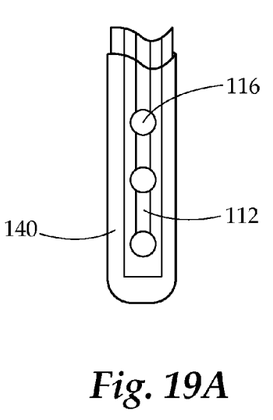
FIGS. 19A-19B illustrate yet embodiment of the monitoring device, wherein the LED arm and the dark sensor photocell arm allows for each of the LED probes and the dark sensor photocells to be located directly on each respective arm.
Figure 19B:
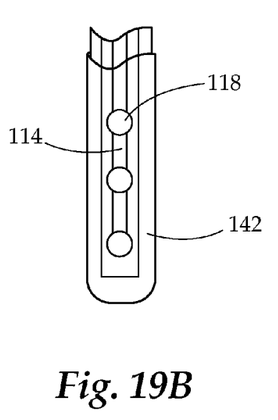

FIGS. 19A-19B illustrate yet embodiment, wherein the LED arm 112 and the dark sensor photocell arm 114 allows for each of the LED probes 116 and the dark sensor photocells 118 to be located directly on each respective arm 112, 114, and then subsequently each arm 112, 114 is encapsulated by a heat shrink transparent plastic cover 140, 142. In this embodiment, the inclusion of the transparent plastic cover 140, 142 over the arms 112, 114 allows not only for the LED probes 116 and the dark sensor photocells 118 submerged in the septic tank and remain clean while submerged in the septic tank. Additionally, this embodiments allows for the transmission of signals between the LED probes 116 and the dark sensor photocells 118. The inclusion of the plastic covers 140, 142 enable the LED probes 116, and the dark sensor photocells 118 to be placed anywhere along the length of the respective arms 112, 114 to allow for different usages and/or operating environments. Moreover, as previously described, this embodiment may include the LED probe 16 further comprises an LED circuit 42. The LED circuit 42 provides power to the LED probes 16 as well as allowing for the transfer of signals (see FIG. 5). Finally, the dark sensor photocell 18 further comprises a dark sensor photocell circuit 44. The dark sensor photocell circuit 44 provides power to the dark sensor photocells 18 as well as allowing for the transfer of signals (see FIG. 6).

Figure 20:
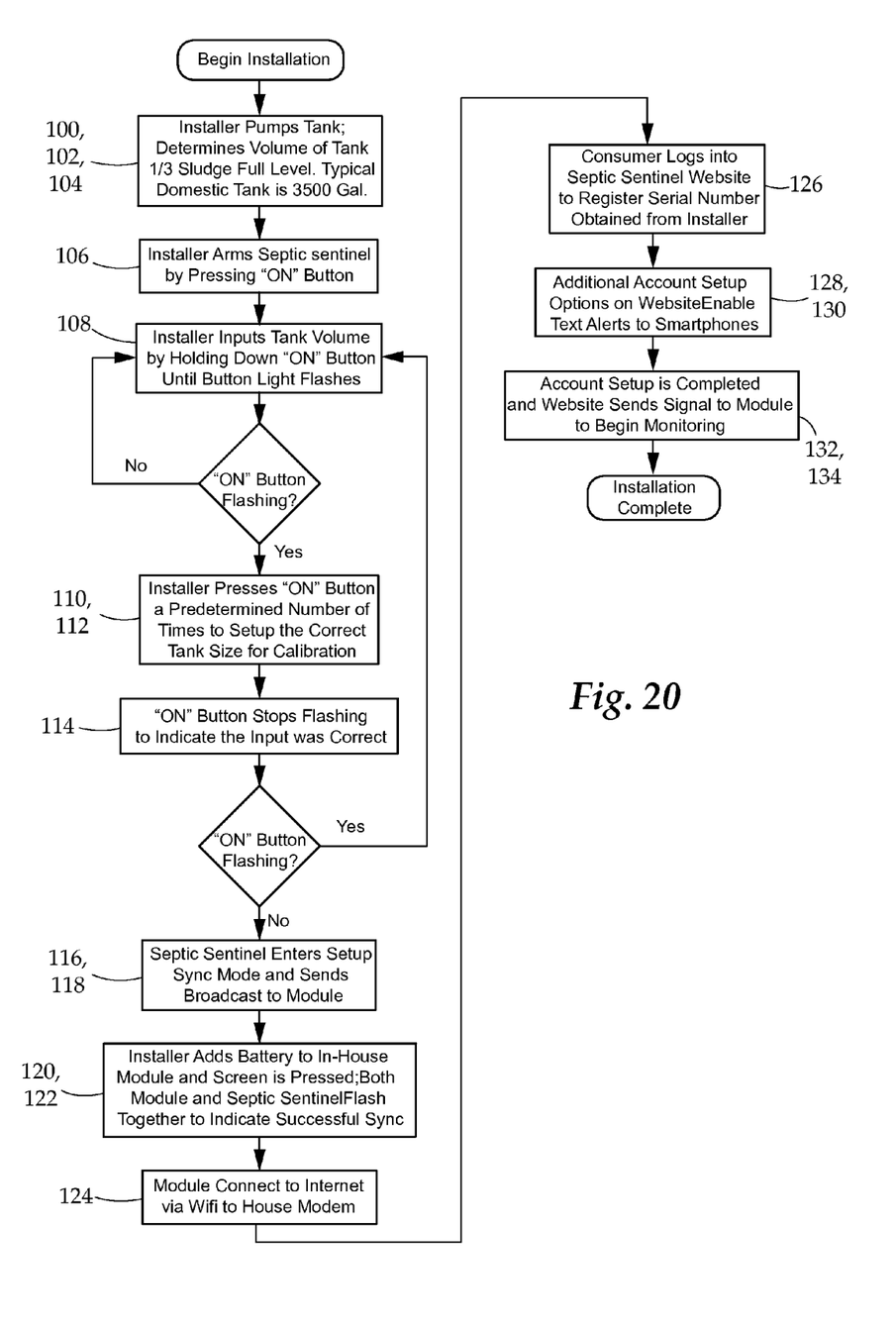
FIG. 20 illustrates a flow diagram of one embodiment for installation of a plurality of monitoring devices within a septic tank system.

FIG. 20 illustrates a block diagram for installation of the instant invention within a septic tank and each respective monitoring device 1. Initially, at step 100, the operator of the system pumps the septic tank where the monitoring device will be installed for use. Once the tank is pumped, at step 102 the operator determines the volume of the septic tank, and then further determines the one-third full level of the septic tank at step 104. Subsequently, at step 106, the operator presses the "ON" button 30 on the monitoring device 1 thereby arming the system. At step 108, the installer holds down the "ON" button 30 until the "ON" button 30 flashes; when the "ON" button 30 flashes the operator continues with the installation of the system. However, when the "ON" button 30 does not flash the system returns to step 108, wherein the operator will again hold down the "ON" button 30 until there is flashing. Once the "ON" button is flashing, the operator of the system identifies a corresponding input signal at step 110 relative to the septic tank size where the monitoring device 1 is being installed and which was measured in step 102. Once the input signal is determined, then at step 112, the operator presses the "ON" button 30 the number of times that correspond to the input signal identified at step 110. When the input signal entered is correct, then at step 114, the "ON" button stops flashing and the operator continues with the installation. Alternatively, when the "ON" button 30 is still flashing the input has not been correctly entered and the system returns to step 108 to hold down the "ON" button to re-start the process of entering the correct septic tank size calibration. Following a correct input signal, at step 116, the system enters a setup sync mode after a successful input. At step 118, the septic tank sludge level monitoring system sends a broadcast to a receiver module 150 (see FIG. 22); at step 120, the operator adds a battery to the receiver module. At step 122, the operator presses the screen on the receiver module causing the module and the "ON" button 30 to flash in unison. Then at step 124, the operator preferably connects the receiver module to a Wi-Fi network. At step 126, operator of the system may visit a website provided by the monitoring device 1 on any internet compatible device. At step 128, the operator enters an accompanying serial number from the manufacturer specifications according to the website instructions. At step 130, the operator may enter preferences on the website according to the instructions, and then at step 132, the operator completes the account setup. Finally, at step 134, the website sends a signal to the receiver module, and at step 136, the monitoring device 1 begins monitoring after receipt of the signal sent in step 134.

Figure 21:
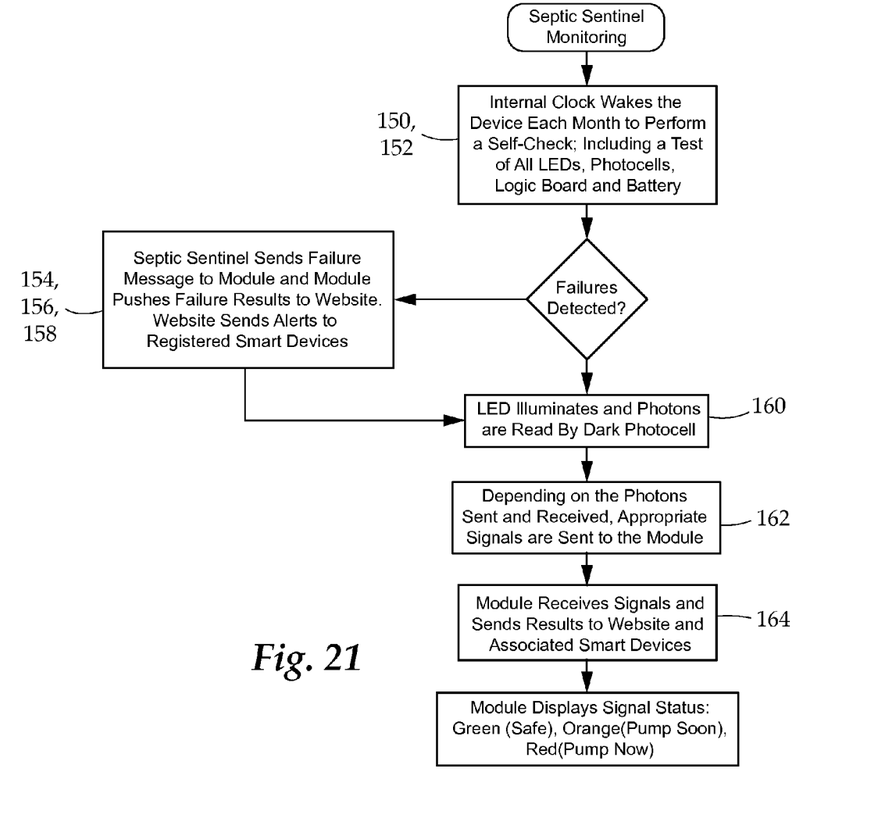
FIG. 21 illustrates a flow diagram of one embodiment for monitoring the levels of sludge in a septic tank utilizing a plurality of monitoring devices.

FIG. 21 illustrates a block diagram for one embodiment for monitoring the sludge levels inside a septic tank utilizing the system described above and at least one monitoring device 1. Initially, at step 150 the monitoring device 1 wakes itself from a lower power state. The intervals at which the system performs the operations at step 150 are predetermined by the operator. At step 152, the monitoring device 1 performs a self-check for failures. When a failure is detected the system proceeds to step 154, wherein the monitoring device 1 transmits a failure message to the receiving module and subsequent at step 156, the receiving module sends the failure message to the website. Next at step 158, the website sends an alert to the registered user device of the operator regarding the failure; conversely, when no failure is detected the system continues the monitoring process. At step 160, the LED sensor 16 illuminates on the sensor arm 12 and is read by the dark photocell sensor 18 on the dark photocell sensor arm 14. At step 162, corresponding signals gathered in step 160 are sent to the receiver module and then at step 164, the receiver module receives the signals sent from the monitoring device 1. At step 166, the receiver module transmits the signals to the website and then at step 168, the website transmits signals to the registered operator device. Finally, at step 170 the receiver module displays a color indicator, wherein a green color indicator indicates a safe state of the septic system, an orange color indicator indicates the system will need to be pumped soon, and a red color indicator indicates the system needs to be pumped immediately.

Figure 22:
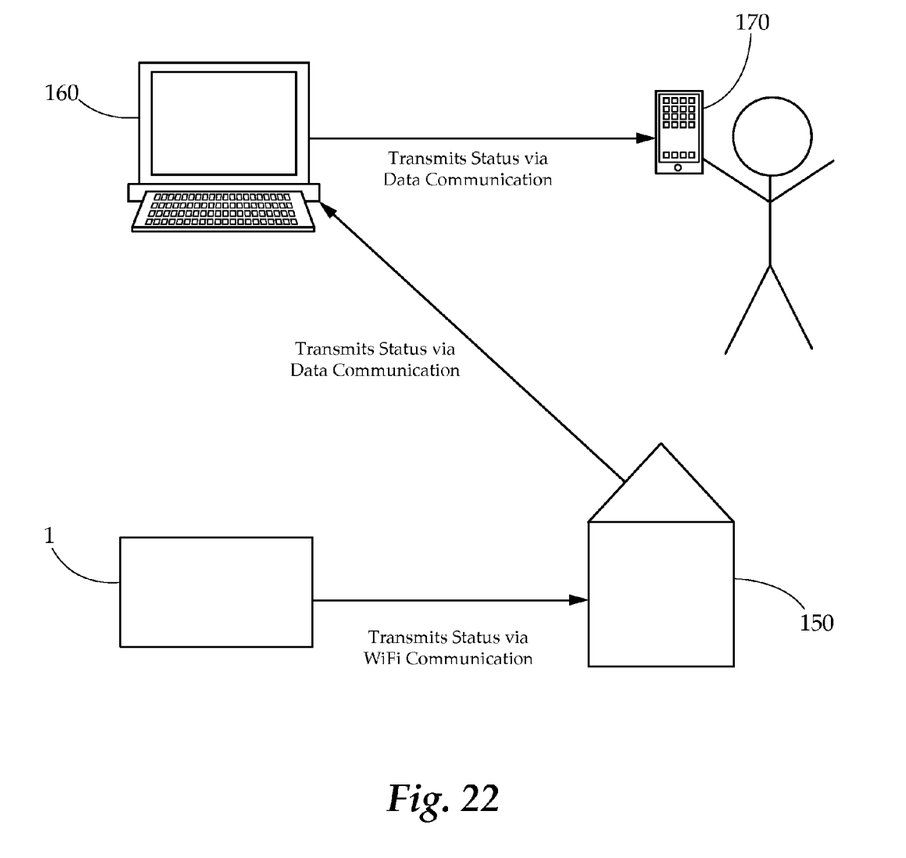
FIG. 22 illustrates a block diagram of one embodiment of a computing system utilizing the monitoring device to monitor the level of sludge in a septic tank.

FIG. 22 illustrates a block system diagram of one embodiment of a computing environment in which the monitoring device 1 preferably operates. In this system, the monitoring device 1 is located a septic tank (not shown) and is in data communication with the receiver module 150 preferably via a wireless-free ("Wi-Fi") connection to transmit readings relating to the depth of sludge and other materials being monitored in the septic tank. Ideally, the receiver module 150 would be located in a corresponding residential home or business that is situated near where the monitoring device 1 and the septic tank is being monitored. The receiver module 150 receives signals from the sensor arms 112, 114. The receiver module 150 is in electronic communication with a computing network 160. In the preferred embodiment the computing network 160 is a website for the septic tank sludge level monitoring system 1. The computer network 160 is additionally in electronic communication with the 170 user device. The receiver module 150 therefore transmits signals to the user device 170 via electronic communication with the computing network 160. Furthermore, the receiver module 150 preferably is in data communication with a computing network 160 that provide a user's account with a status update on the monitoring of the septic tank. Finally, the computing network 160 transmits a message via data communication to a user's assigned mobile device 170 to provide status updates to the user on whether or not the septic tank has reached capacity or is still operating a reasonably safe level.

In conclusion, herein is presented a septic tank sludge level monitoring system. The invention is illustrated by example in the drawing figures, and throughout the written description. It should be understood that numerous variations are possible, while adhering to the inventive concept. Such variations are contemplated as being a part of the present invention.

What is claimed is:

1. A device for monitoring the level of sludge in a septic tank system comprising:
a base unit;
a probe arm, wherein the probe arm extends downwardly from the base unit and further comprises:
a light emitting diode arm;
a dark sensor photocell arm;
wherein the base unit further comprises:
an inner radius;
a cavity; and
wherein the inner radius of the base unit possesses a radius substantially equal to a radius of a corresponding pipe to which the monitoring device is affixed in order to create a snap between the pipe and the monitoring device.

2. The device of claim 1, wherein the light emitting diode arm further comprises:
a plurality of light emitting diode probes.

3. The device of claim 2, wherein the dark sensor photocell arm further comprises:
a plurality of dark sensor photocells.

4. The device of claim 3, wherein each dark sensor photocell is paired with a corresponding light emitting diode probe.

5. The device of claim 4, wherein the light emitting diode arm and the dark sensor photocell arm each further comprise:
a plurality of windows, wherein the plurality of windows are placed along the respective arm and allows for each of the light emitting diode probes and the dark sensor photocells to be submerged in the septic tank and be able to transmit through each window.

6. The device of claim 4, wherein the light emitting diode arm and the dark sensor photocell arm are each encapsulated by a transparent plastic cover to allow the light emitting diode probes and the dark sensor photocells to be placed anywhere along the length of the respective arms.

7. The device of claim 1, wherein the light emitting diode arm and the dark sensor photocell arm are oriented parallel to one another and extend vertically downward from the base unit.

8. The device of claim 1, wherein the light emitting diode arm and the dark sensor photocell arm are positioned within the septic tank at a level that is equivalent to the septic tank being one third full of sludge.

9. The device of claim 1, wherein the light emitting diode arm and the dark sensor photocell arm each contain a plurality of circuit wires to transmit a signal and alarm remotely to an individual operator.

10. The device of claim 1, wherein the base unit further comprises:
   an on button; and
   an indicator light emitting diode, wherein the indicator light emitting diode is illuminated when the monitoring device is powered.

11. A method for monitoring the level of sludge inside a septic tank utilizing at least one device of claim 1, comprising the steps of:
   waking each device from a lower power state;
   performing a self-check by each device for failures;
   illuminating a light emitting diode on a sensor arm;
   reading the light emitting diode by a dark photocell sensor arm;
   transmitting the corresponding signals from each device to receiver module;
   transmitting the signals from the receiver module to a computing network; and
   displaying a color indicator on the receiver module to indicate the status of the level of sludge in the septic system.

12. A system for monitoring the level of sludge in a septic tank utilizing a plurality of devices of claim 1 wherein each monitoring device is affixed to a corresponding pipe within the septic tank, comprising:
   a receiver module, wherein the receiver module is in data communication with each monitoring device;
   a computing network, wherein the computing network is in electronic communication with the receiver module; and
   a user device, wherein the user device is in electronic communication with the computer network and assigned by an operator of the system.

13. The system of claim 12, wherein each monitoring device further comprises:
   wherein the base unit further comprises:
      an on button; and
   wherein the light emitting diode is illuminated when the monitoring device is powered;
   wherein the light emitting diode arm and the dark sensor photocell arm each further comprise:
   a plurality of windows, wherein the plurality of windows are placed along the respective arm and allows for each of the light emitting diode probes and the dark sensor photocells to be submerged in the septic tank and be able to transmit through each window.

14. The system of claim 13, wherein the computing network transmits a message via data communication to the assigned user device to provide status updates on the level of sludge in the septic tank being monitored.

* * * * *